United States Patent
Thiel et al.

(10) Patent No.: US 10,588,494 B2
(45) Date of Patent: Mar. 17, 2020

(54) CAMERA AND METHOD FOR THE THREE-DIMENSIONAL MEASUREMENT OF A DENTAL OBJECT

(71) Applicant: SIRONA DENTAL SYSTEMS GMBH, Bensheim (DE)

(72) Inventors: Frank Thiel, OberRamstadt (DE); Joachim Pfeiffer, Bensheim (DE)

(73) Assignee: DENTSPLY SIRONA INC., York, PA (US)

( * ) Notice: Subject to any disclaimer, the term of this patent is extended or adjusted under 35 U.S.C. 154(b) by 0 days.

(21) Appl. No.: 15/575,858

(22) PCT Filed: May 20, 2016

(86) PCT No.: PCT/EP2016/061368
§ 371 (c)(1),
(2) Date: Nov. 21, 2017

(87) PCT Pub. No.: WO2016/188879
PCT Pub. Date: Dec. 1, 2016

(65) Prior Publication Data
US 2018/0125337 A1 May 10, 2018

(30) Foreign Application Priority Data
May 22, 2015 (DE) .......................... 10 2015 209 410

(51) Int. Cl.
*A61B 1/00* (2006.01)
*A61C 9/00* (2006.01)
(Continued)

(52) U.S. Cl.
CPC ...... *A61B 1/00172* (2013.01); *A61B 1/00186* (2013.01); *A61B 1/00188* (2013.01);
(Continued)

(58) Field of Classification Search
CPC ............................ A61B 1/00186; A61C 9/006
USPC ........................................................ 348/77
See application file for complete search history.

(56) References Cited

U.S. PATENT DOCUMENTS 5,372,502 A * 12/1994 Massen ............... A61C 13/0004
433/215
2015/0321644 A1* 11/2015 Kosubek ............... B60S 1/0844
348/148
(Continued)

FOREIGN PATENT DOCUMENTS

WO   2010145669 A1   12/2010
WO   2012083967 A1   6/2012
(Continued)

OTHER PUBLICATIONS

International Search Report; PCT/EP2016/061368; Sep. 13, 2016 (completed); dated Sep. 27, 2016.
(Continued)

*Primary Examiner* — Joseph G Ustaris
*Assistant Examiner* — Amir Shahnami
(74) *Attorney, Agent, or Firm* — Dentsply Sirona Inc.

(57) ABSTRACT

The invention relates to a method and a camera for the three-dimensional measurement of a dental object, comprising at least one light source that emits an illumination beam, at least one projection mask that produces a projection pattern, focusing optics that display the projection pattern in a plane of sharp focus at a defined focal distance relative to the dental camera. The projection pattern projected onto the object is reflected by the object as an observation beam and is acquired by means of a sensor. During the measurement of the object, the focusing optics are controlled in such a way that the focal distance of the plane of sharp focus relative to the camera is adjusted incrementally between a number of defined scan positions.

13 Claims, 2 Drawing Sheets

(51) Int. Cl.
  *A61B 1/04*   (2006.01)
  *A61B 1/06*   (2006.01)
  *A61B 1/247*  (2006.01)
  *G01B 11/25*  (2006.01)
  *G01B 11/24*  (2006.01)

(52) U.S. Cl.
  CPC ............ *A61B 1/042* (2013.01); *A61B 1/0669* (2013.01); *A61B 1/0684* (2013.01); *A61B 1/247* (2013.01); *A61C 9/006* (2013.01); *G01B 11/2509* (2013.01); *G01B 11/24* (2013.01)

(56) References Cited

U.S. PATENT DOCUMENTS

2016/0022389 A1* 1/2016 Esbech ................... G01J 3/513
                                                    250/208.1
2016/0156888 A1* 6/2016 Euler ................. G01B 11/2509
                                                    348/744

FOREIGN PATENT DOCUMENTS

WO    2014125037 A1   8/2014
WO    2014202442 A1   12/2014

OTHER PUBLICATIONS

Written Opinion of the International Searching Authority; PCT/EP2016/061368; Sep. 13, 2016 (completed); dated Sep. 27, 2016.
International Preliminary Report on Patentability; PCT/EP2016/061368; Sep. 13, 2016 (completed); dated Sep. 27, 2016.

* cited by examiner

CAMERA AND METHOD FOR THE THREE-DIMENSIONAL MEASUREMENT OF A DENTAL OBJECT

TECHNICAL FIELD

The invention relates to a camera for the three-dimensional measurement of a dental object, comprising at least one light source that emits an illumination beam, at least one projection mask that produces a projection pattern, focusing optics that display the projection pattern in a plane of sharp focus at a defined focal distance relative to the dental camera, wherein the projection pattern projected onto the object is reflected by the object as an observation beam and is acquired by means of a sensor.

BACKGROUND OF THE INVENTION

A number of methods and cameras for the three-dimensional measurement of dental objects are known from the state of the art.

WO 2014/125037 A1 discloses a measuring device for the measurement of surfaces and a surface color of an object, wherein a multi-color light source, a color sensor and a data processing system are used to calculate a three-dimensional model of the object from a plurality of 2D images.

WO 2014/202442 A1 discloses a measuring device for color-coded triangulation, wherein a pattern is projected onto the object and measured in a plurality of spectral regions by means of a sensor. A plurality of color filters for the individual spectral ranges is disposed in front of the sensor.

WO 2012/083967 A1 discloses a device for optical 3D measurement of an object using an optical confocal measurement method, wherein, in addition to a first light source, at least one second light source is used, the light of which is coupled into the beam path of the device using a light guide. It is furthermore disclosed that the light sources, such as color LEDs or LEDs, can be used in combination with color filters, whereby the light sources are switched on in an alternating manner to ensure homogeneous illumination.

WO 2010/145669 A1 discloses a device for optical 3D measurement of an object using an optical confocal measurement method. In this case, a temporally changing pattern is projected onto the object. The changing pattern is generated with the aid of a motor-driven mechanical means in the form of a wheel.

One disadvantage of these methods is that the temporally changing projection pattern is generated using movable projection means in the illumination beam path, such as a motor-driven, wheel-shaped projection grating. Incorrect control or incorrect actuation of the mechanically driven projection gratings can cause positioning errors, as a result of which incorrect three-dimensional image data of the object is obtained.

Another disadvantage is that said methods allow only a three-dimensional measurement of the object, and not a color measurement.

The task of the present invention is therefore to provide a camera, which is of compact design and allows an error-free measurement of the dental object and a color measurement.

SUMMARY OF THE INVENTION

The invention relates to a camera for the three-dimensional measurement of a dental object, comprising at least one light source that emits an illumination beam, at least one projection mask that produces a projection pattern, focusing optics that display the projection pattern in a plane of sharp focus at a defined focal distance relative to the dental camera, wherein the projection pattern projected onto the object is reflected by the object as an observation beam and is acquired by means of a sensor. During the measurement of the object, the focusing optics are controlled in such a way that the focal distance of the plane of sharp focus relative to the camera is adjusted incrementally between a number of defined scan positions.

An observation mask is disposed in the beam path of the observation beam in front of the sensor, wherein the observation mask is fixedly aligned relative to the projection mask. The projection mask consists of a plurality of projection pattern elements containing a variety of color filters. The observation mask likewise consists of a plurality of observation mask elements containing a variety of color filters.

The adjustment of the focusing optics can be carried out continuously, whereby only the image data of the images is read discretely at the defined scan positions.

The camera can be integrated into a conventional housing in the form of a handpiece. The light source can be a white LED, or a group of colored LEDs, for example, that emits an illumination beam with a broad spectrum. The projection means can be a grating consisting of a plurality of color filters or a colored digital light projector made of liquid-crystal elements (LCD), which is controlled as appropriate and produces the projection pattern. The focusing optics are adjustable and focus the projection pattern onto the established plane of sharp focus, whereby the plane of sharp focus is varied incrementally so that the entire object can be scanned. The scan positions can, for example, have a distance of 0.1 mm from one another.

The present camera operates according to a method that represents a combination of a depth-scanning confocal three-dimensional measurement method and a color matrix. With respect to the arrangement of the color filters, the projection mask can match the observation mask, whereby a projection mask element or the corresponding illumination mask element can correspond to one single pixel of the sensor or, for example, to a 2×2 group of four pixels or, for example, to a 3×3 group of nine pixels of the sensor. If then, the projection pattern is displayed in sharp focus and the position of the sharp layer coincides with the object surface of the object, an intensity value for a specific pixel reaches its maximum, whereby the surrounding observation mask elements exhibit a different color relative to said pixel. If the projection pattern is blurred and the position of the object surface does not coincide with the position of the sharp layer, the object appears blurred in the images. The intensity value then decreases for every observation mask element, whereby the observation beams that escape the boundaries of the observation mask element are blocked, because the color filters of the surrounding observation mask elements exhibit a different color.

This results in an intensity profile in one pixel that is similar to a confocal intensity profile, i.e. the intensity in one pixel as a function of the focal position reaches its maximum when the object position corresponds to the focus position.

Alternatively, the local spatial contrast of a pixel can be determined in a manner similar to a depth from focus approach. This can be achieved by evaluating the intensity of a pixel relative to the intensities of the adjacent pixels. Therefore, if the object is disposed in the focal position, the local contrast will reach its maximum.

As a result, a local contrast of a signal curve of the intensity value as a function of the focal distance, and thus the ratio between a signal maximum and a signal background, is improved.

Another advantage of this camera is that a color measurement of the object surface is made possible by evaluating the intensity values for the individual observation mask elements.

The dimensions of an image of a specific projection mask element of the projection pattern in the plane of the observation mask can advantageously correspond to the dimensions of a corresponding observation mask element, wherein a color filter in the projection mask element and a color filter in the corresponding observation mask element at least partially allow a coinciding spectral range to pass through.

Therefore only the observation beams of the projection pattern that are disposed within the corresponding observation element reach the sensor, whereby the observation beams that escape the boundaries of the observation mask element are blocked, because the surrounding observation mask elements exhibit a different color and thus allow only a different spectral range to pass through.

The light source can advantageously be a white LED, or a combination of a number of colored LEDs, that emits a wide color spectrum.

As a result, the light source can emit an illumination beam with a broad spectrum, for example with a spectrum similar to daylight.

The projection mask and/or the observation mask can advantageously be constructed from a plurality of optical color filters, or be a colored digital light projector comprising liquid-crystal elements (LCD) that produces the individual colored projection mask elements of the projection pattern.

Any shape of projection pattern with the desired arrangement of the colored pattern elements can thus be produced by means of the projection mask and/or by means of the observation mask.

The projection mask and/or the observation mask can advantageously comprise a checkerboard-like pattern, wherein the square projection mask elements and/or the square observation mask elements are disposed adjacent to one another without gaps.

As a result, every projection mask element or every observation mask element in the imaging plane of the sensor corresponds to the dimensions of a single pixel or to the dimensions of a square pixel group of four or nine pixels. Consequently, an intensity value associated with a specific observation mask element can be read for every pixel.

The projection mask and/or the observation mask can advantageously consist of blue, green, yellow and red color filters, whereby a square group of four comprises a blue color filter, a green color filter, a yellow color filter and a red color filter, so that every color filter does not have an adjacent color filter in the same color.

As a result, the color spectra of the individual color filters do not overlap, so that the four color channels can be evaluated separately. On the basis of the intensity values of the individual observation mask elements in said primary colors, a color of the respective region of the object surface can be determined as well.

The projection mask and/or the observation mask can advantageously be dimensioned and aligned in such a way that every projection mask element of the projection pattern and/or every corresponding observation mask element is projected onto one pixel of the sensor, so that the projected image of the pattern element in the plane of the sensor corresponds to the dimensions of the pixel.

As a result, the evaluation and the determination of the intensity values are simplified. The reason for this is that every pixel in this design is assigned to an observation mask element.

The projection mask and/or the observation mask can advantageously be dimensioned and aligned in such a way that every projection mask element of the projection pattern and/or every corresponding observation mask element is projected onto one square pixel group consisting of four pixels of the sensor, so that the projected image of the projection mask element and/or the observation mask element corresponds to the dimensions of said pixel group.

This does reduce the resolution in comparison to the mentioned alternative. But the light sensitivity is improved, as a result of which the exposure times can be decreased.

During the measurement of the object, an image can advantageously be taken in every scan position, wherein an intensity value is determined for every projection mask element and/or for every corresponding observation mask element by means of this image.

The intensity value is thus directly determined by reading the individual pixels. The sensor can be a CCD sensor or a CMOS sensor.

By means of an arithmetic unit and using the intensity value as a function of the focal distance, depth information of an object surface of the object can advantageously be determined for every projection mask element and/or for every corresponding observation mask element, thus allowing the measurement of three-dimensional surface data of the object.

The intensity value is thus determined as a function of the focal distance for every observation mask element. A focal distance at the maximum of the intensity value, which corresponds to the focal distance of the object surface for the respective observation mask element, can subsequently be obtained by means of the arithmetic unit. In this way, the complete three-dimensional surface data can be generated.

Using the intensity values of at least four adjacent projection mask elements, a color value can advantageously be acquired by means of the arithmetic unit, so that a color measurement of the dental object is obtained.

The color measurement of the object is thus made possible by using the individual intensity values of different color filters. The three-dimensional measurement by means of the abovementioned camera is thus performed according to this method.

One advantage of this method is that the three-dimensional measurement is performed by means of the projection mask and the observation mask, which are aligned with respect to one another, without the need for mechanically movable components.

A further advantage is that, in addition to the three-dimensional measurement, a color measurement of the object is made possible as well.

The invention further relates to a method for the three-dimensional measurement of a dental object by means of a camera, comprising at least one light source that emits an illumination beam, at least one projection mask that produces a projection pattern, focusing optics that display the projection pattern in a plane of sharp focus at a defined focal distance relative to the dental camera, wherein the projection pattern projected onto the object is reflected by the object as an observation beam and is acquired by means of a sensor. During the measurement of the object, the focusing optics are controlled in such a way that the focal distance of the plane of sharp focus relative to the camera is adjusted incrementally between a number of defined scan positions. An observation mask is disposed in the beam path of the observation beam in front of the sensor, wherein the observation mask is fixedly aligned relative to the projection mask. The projection mask consists of a plurality of projection pattern elements containing a variety of color filters. The observation mask likewise consists of a plurality of observation mask elements containing a variety of color filters. The projection pattern reflected by the object thus passes through the color filters of the observation mask before being acquired by means of the sensor.

This method therefore allows the measurement of the dental object by means of the above-described camera.

One advantage of this method is therefore that the three-dimensional measurement of the object without moving parts is made possible. This improves the error susceptibility of the system.

A further advantage of this method is that, in addition to the three-dimensional measurement, a color measurement of the object is made possible.

The dimensions of an image of a specific projection mask element of the projection pattern in the plane of the observation mask can advantageously correspond to the dimensions of a corresponding observation mask element. The color filters in the projection mask element and in the corresponding observation mask element can thereby at least partially allow a coinciding spectral range to pass through.

The observation beams within an observation mask element are therefore allowed to pass through to the respective pixel of the sensor, whereby the observation beams for this observation mask element that escape the boundaries of the observation mask element as a result of blurry imagining are blocked, because the surrounding color filters exhibit a different color.

The light source can advantageously be a white LED, or a combination of a number of colored LEDs, that emits a wide color spectrum.

As a result, the light source can emit a wide spectrum, i.e. a spectrum similar to daylight.

The projection mask and/or the observation mask can advantageously comprise a checkerboard-like pattern, wherein the square projection mask elements and/or the square observation mask elements are disposed adjacent to one another without gaps.

The grid-like arrangement of the projection mask and/or the observation mask coincides with the arrangement of the pixels on the sensor.

The projection mask and/or the observation mask can advantageously consist of blue, green, yellow and red color filters, whereby a square group of four comprises a blue color filter, a green color filter, a yellow color filter and a red color filter, so that every color filter does not have an adjacent color filter in the same color.

The colored channels with the primary colors are therefore evaluated independently of one another, whereby every color filter does not have an adjacent color filter in the same color. As a result, the observation beams outside said color filter are blocked.

The projection mask and/or the observation mask can advantageously be dimensioned and aligned in such a way that every projection mask element of the projection pattern and/or every corresponding observation mask element is projected onto one pixel of the sensor, so that the projected image of the pattern element in the plane of the sensor corresponds to the dimensions of the pixel.

The read intensity value of a pixel therefore corresponds to a single observation mask element. The evaluation and the determination of the depth information of the object are thus simplified.

During the measurement of the object, an image can advantageously be taken in every scan position, wherein an intensity value is determined for every projection mask element and/or for every corresponding observation mask element by means of this image.

By means of an arithmetic unit and using the intensity value as a function of the focal distance, depth information of an object surface of the object can advantageously be obtained for every projection mask element and/or for every corresponding observation mask element, thus allowing the measurement of three-dimensional surface data of the object.

The focal distance at the maximum of the intensity value is thus determined, whereby said focal distance corresponds to the depth information of the object surface in the region of said observation mask element.

Using the intensity values of at least four adjacent projection mask elements, a color value can advantageously be acquired by means of the arithmetic unit, so that a color measurement of the dental object is obtained.

A color measurement in addition to the three-dimensional measurement is therefore made possible in a quick and easy way. A color value, which corresponds to the color value in the region of the respective object surface, can therefore be calculated on the basis of the ratios of the primary colors of the adjacent color filters.

BRIEF DESCRIPTION OF THE DRAWINGS

The invention is explained with reference to the drawings. The drawings show.

DETAILED DESCRIPTION OF THE INVENTION

Figure 1:
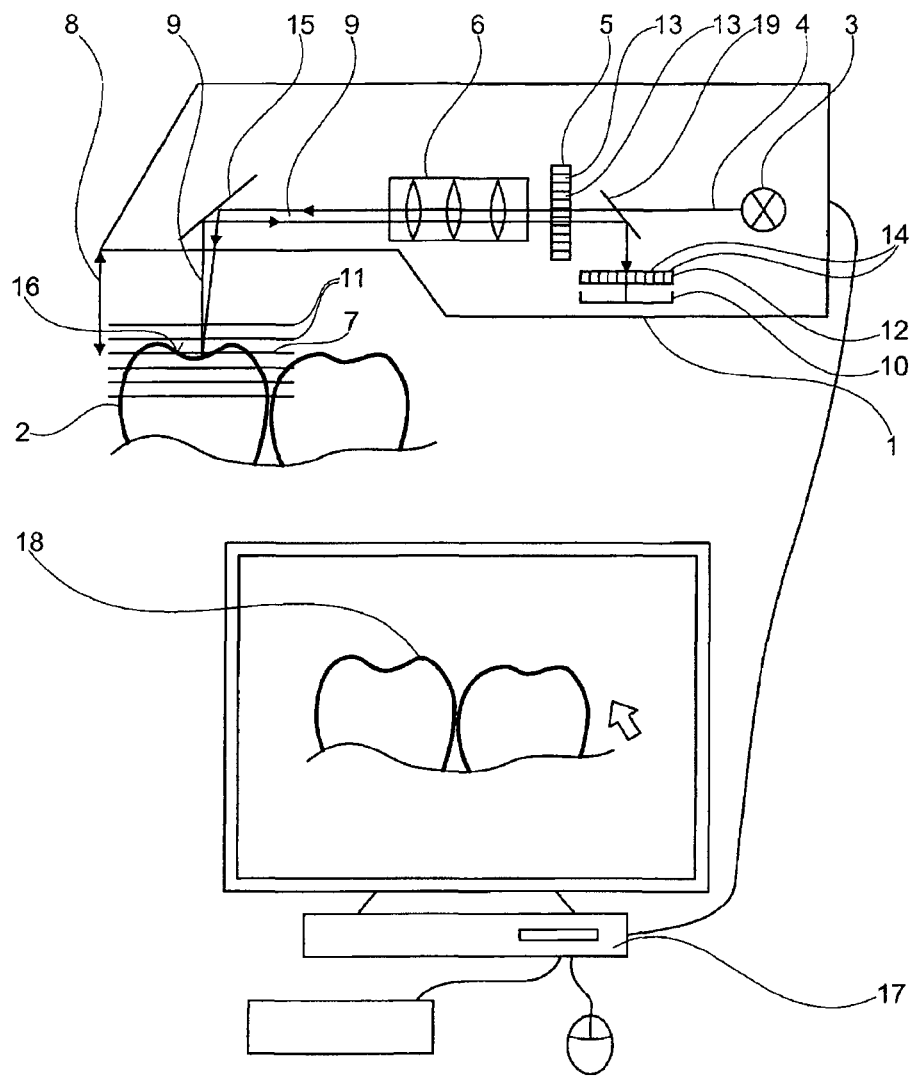
FIG. 1 shows a sketch of a camera for the three-dimensional measurement of a dental object.

FIG. 1 shows a sketch of a camera 1 for the three-dimensional measurement of a dental object 2, such as a tooth, wherein the camera comprises at least one light source 3 that emits an illumination beam 4. The light source 3 can for example be a white LED, or a combination of a number of colored LEDs, that emits a wide color spectrum.

The camera further comprises a projection mask 5, which produces a projection pattern. Focusing optics 6 display the illumination beams 4 in sharp focus in a plane of sharp focus 7 at a defined focal distance 8 relative to the dental camera 1. The projected projection pattern is reflected by the object 2 as an observation beam 9, whereby the observation beam 9 is acquired by means of a sensor 10, such as a CCD sensor or a CMOS sensor. During the measurement of the object, i.e. during the scanning procedure, the focusing optics 6 are controlled in such a way that the focal distance 8 of the plane of sharp focus 7 relative to the camera 1 is adjusted incrementally between a number of defined scan positions 11, which are represented as parallel lines. An observation mask 12 is disposed in the beam path of the observation beam 9 in front of the sensor 10, wherein the observation mask 12 is fixedly aligned relative to the projection mask 5. The projection mask 5 is constructed from a plurality of color filters 13 of different colors. The observation mask is likewise constructed from a plurality of color filters 14 of different colors. The illumination beam 4 is deflected towards the object 2 by means of a beam splitter 15. The arrangement of the color filters 13 and the projection mask 5 corresponds to the arrangement of the color filters 14 in the observation mask so that, if the projection pattern is displayed in sharp focus and the position of the sharp layer 7 coincides with a surface 16 of the object 2, an intensity value of a corresponding pixel or pixel group on the sensor 10 reaches its maximum, because the surrounding color filters 14 of the observation mask 12 exhibit a different color. If the projection pattern is blurred and the position of the surface 16 of the object 2 does not coincide with the position of the sharp layer 7, the object appears blurred in the images, as a result of which the intensity value decreases.

This is due to the fact that the observation beams that escape the boundaries of the observation mask element are blocked by the adjacent color filters 14 of a different color. The intensity value for every pixel is thus measured as a function of the focal distance, so that depth information of the surface 16 of the object can be obtained for every pixel. By means of an arithmetic unit 17, such as a computer, a three-dimensional model 18 of the entire object 2 is thus calculated on the basis of the image data of the sensor 10. In addition to the three-dimensional measurement, the evaluation of the intensity values of the individual color filters makes a color measurement of the surface 16 of the object 2 possible as well.

Figures 2, 3:
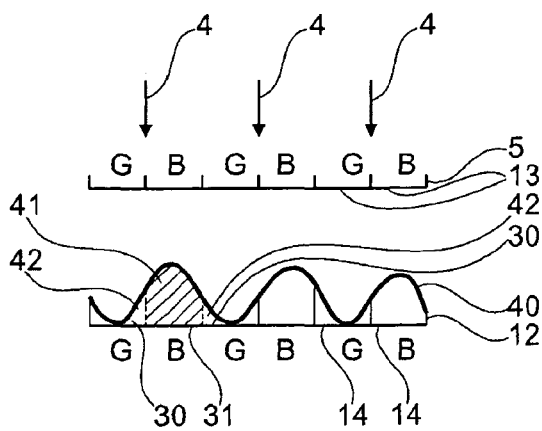
FIG. 2 shows a sketch of the projection mask with a plurality of color filters.
FIG. 3 shows a sketch to illustrate the structure of the observation mask made of a plurality of color filters.

FIG. 2 shows a sketch of the projection mask 5 with a schematic structure consisting of a plurality of color filters 13. The color filters are arranged in square groups of four consisting of a green color filter 20, labeled with G, a blue color filter 21, labeled with a B, a yellow color filter 22, labeled with a Y and a red color filter 23, labeled with an R.

As a result, every color filter 13 does not have an adjacent color filter in the same color.

The observation beam 9 passes through the focusing optics 6 and is deflected toward the sensor 10 by means of the beam splitter 19.

FIG. 3 shows a sketch to illustrate the structure of the observation mask 12 of FIG. 1 consisting of a plurality of color filters 14, wherein the arrangement of the green color filters 30, the blue color filters 31, the yellow color filters 32 and the red color filters 33 matches the arrangement of the projection mask 5 of FIG. 2.

Figure 4:
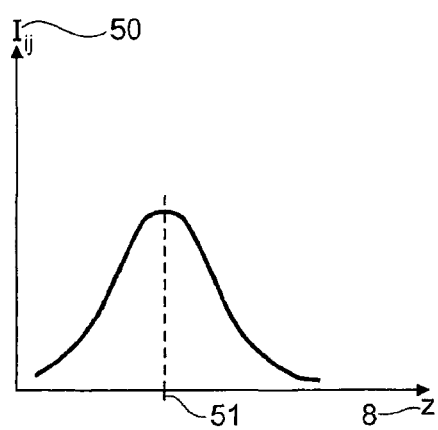
FIG. 4 shows a sketch of a lateral view of the projection mask.

FIG. 4 shows a sketch of a lateral view of the projection mask 5 with the color filters 13 and the observation mask 12 with the color filters 14 to illustrate the functional principle of the present method. The illumination beams 4 with a broadband spectrum strike the projection mask, whereby an intensity distribution 40 of the blue spectrum is shown schematically. In the present case, the projection pattern is displayed in a blurred manner, because the sharp layer does not coincide with the surface 16 of the object 2 of FIG. 1; only a first portion 41, which is shown as a dotted line, arrives at the blue filter 31 of the observation mask 12. A second portion 42 of the intensity of the blue light is blocked by the adjacent green color filters 30, so that the intensity of the blue channel reaches a maximum if the projection pattern is displayed in sharp focus and decreases if the image is blurred. The intensity values are thus determined as a function of the focal distance 8 for each channel, i.e. for the green, blue, yellow and red color filters.

Figures 5, 6:
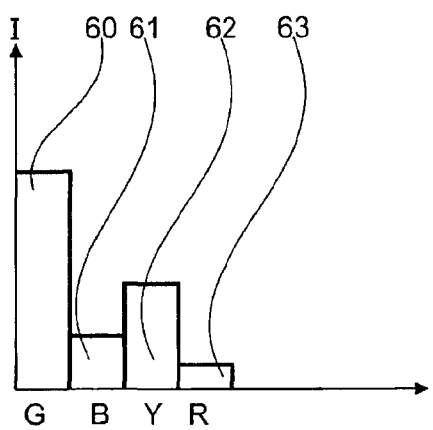
FIG. 5 shows an intensity value of a specific observation mask element.
FIG. 6 shows a sketch of the intensity values of a group of four of the color filters of the observation mask.

FIG. 5 shows an intensity value 50 of a specific observation mask element, such as a green, blue, yellow or red color filter, of the observation mask 12 as a function of the focal distance 8, wherein the profile of the intensity value exhibits a maximum 51, which lies within the sharp layer and thus represents depth information for the respective measuring point on the surface 16 of the object 2. The individual depth information for all measuring points of the object 2 is obtained in this manner, and the three-dimensional model 18 of FIG. 1 is calculated.

FIG. 6 shows a sketch of the intensity values of a group of four of the color filters 30, 31, 32 and 33 of the observation mask 12 of FIG. 3. The color of the surface 16 of the object 2 at a specific measuring point can then be determined from a first intensity value 60 of the green color filter 30, a second intensity value 61 of the blue color filter 31, a third intensity value 62 of the yellow color filter 32 and a fourth intensity value 63 of the red color filter 33. A complete color measurement of the object 2 can thus be performed.

REFERENCE SIGNS 1 camera
2 object
3 light source
4 illumination beam
5 projection mask
6 focusing optics
7 plane of sharp focus
8 focal distance
9 observation beam
10 sensor
11 clamping position
12 observation mask
13 color filter
14 color filter
15 beam splitter
16 surface
17 arithmetic unit
18 beam splitter
20 green color filter
21 blue color filter
22 yellow color filter
23 red color filter
30 green color filter
31 blue color filter
32 yellow color filter
33 red color filter
40 intensity distribution
41 first portion
42 second portion
50 intensity value
51 maximum of the intensity value
60 first intensity value
61 second intensity value
62 third intensity value
63 fourth intensity value

The invention claimed is:

1. A camera for the three-dimensional measurement of a dental object, comprising at least one light source that emits an illumination beam, at least one projection mask that produces a projection pattern, focusing optics that display the projection pattern in a plane of sharp focus at a defined focal distance relative to the camera, wherein the projection pattern projected onto the object is reflected by the object as an observation beam and is acquired by means of a sensor,
- wherein during the measurement of the object, the focusing optics are controlled in such a way that the focal distance of the plane of sharp focus relative to the camera is adjusted incrementally between a number of defined scan positions,
- wherein an observation mask is disposed in the beam path of the observation beam in front of the sensor,
- wherein the observation mask is fixedly aligned relative to the projection mask,
- wherein the projection mask includes a plurality of projection pattern elements having a variety of color filters,
- wherein the observation mask includes a plurality of observation mask elements having a variety of color filters,
- wherein an arrangement of the color filters on the projection mask matches another arrangement of the color filters on the observation mask
- wherein dimensions of an image of a specific projection mask element of the projection pattern in the plane of the observation mask correspond to dimensions of a corresponding observation mask element,
- wherein a color filter in the projection mask element and a color filter in the corresponding observation mask element at least partially allow a coinciding spectral range to pass through such that parts of the observation beam of the projection pattern that are disposed within the corresponding observation mask element reach the sensor and/or parts of the observation beam that escape boundaries of the corresponding observation mask element are blocked from reaching the sensor.

2. The camera according to claim 1 wherein the light source is a white LED, or a combination of a number of colored LEDs, that emits a wide color spectrum.

3. The camera according to claim 1, wherein the projection mask and/or the observation mask includes a plurality of optical color filters or is a colored digital light projector having liquid-crystal elements (LCD), which produces the individual colored projection mask elements of the projection pattern.

4. The camera according to claim 1, wherein the projection mask and/or the observation mask comprises a checkerboard-like pattern, wherein square projection mask elements and/or square observation mask elements are disposed adjacent to one another without gaps.

5. The camera according to claim 4, wherein the projection mask and/or the observation mask includes blue, green, yellow and red color filters,
- wherein a square group of four comprises a blue color filter, a green color filter, a yellow color filter and a red color filter so that every color filter does not have an adjacent color filter in the same color.

6. The camera according to claim 1, wherein the projection mask and/or the observation mask is dimensioned and aligned in such a way that every projection mask element of the projection pattern and/or every corresponding observation mask element is projected onto one pixel of the sensor, so that the projected image of the pattern element in the plane of the sensor corresponds to the dimensions of the pixel.

7. The camera according to claim 1, wherein the projection mask and/or the observation mask is dimensioned and aligned so that every projection mask element of the projection pattern and/or every corresponding observation mask element is projected onto one square pixel group having four pixels of the sensor, so that the projected image of the projection mask element and/or the observation mask element corresponds to the dimensions of said pixel group.

8. The camera according to claim 1, wherein, during the measurement of the object, an image is taken in every scan position,
- wherein an intensity value is determined for every projection mask element and/or for every corresponding observation mask element by means of this image.

9. The camera according to claim 8,
- wherein, by means of an arithmetic unit and using the intensity value as a function of the focal distance, depth information of an object surface of the object is determined for every projection mask element and/or for every corresponding observation mask element, thus making it possible to measure the three-dimensional surface data of the object.

10. The camera according to claim 1,
- wherein, with the aid of the arithmetic unit and using the intensity values of at least four adjacent projection mask elements, a color value is generated, so that a color measurement of the dental object is obtained.

11. A method for the three-dimensional measurement of a dental object using a camera, comprising
- emitting an illumination beam from at least one light source,
- producing a projection pattern from at least one projection mask,
- displaying the projection pattern in a plane of sharp focus at a defined focal distance relative to the camera using focusing optics,
- reflecting as an observation beam, the projection pattern projected onto the dental object,
- acquiring said reflected projection pattern using a sensor,
- controlling the focusing optics in such a way that the focal distance of the plane of sharp focus relative to the camera is adjusted incrementally between a number of defined scan positions,
- disposing an observation mask in the beam path of the observation beam in front of the sensor,
- aligning the observation mask relative to the projection mask,
- wherein the projection mask includes a plurality of projection pattern elements containing a variety of color filters, wherein the observation mask likewise includes a plurality of observation mask elements containing a variety of color filters, wherein the color filters on the projection mask are arranged to match the color filters on the observation mask,
- wherein dimensions of an image of a specific projection mask element of the projection pattern in a plane of the observation mask correspond to dimensions of a corresponding observation mask element,
- wherein a color filter in the projection mask element and a color filter in the corresponding observation mask element at least partially allow a coinciding spectral range to pass through such that parts of the observation beam of the projection pattern that are disposed within the corresponding observation mask element reach the sensor and/or parts of the observation beam that escape boundaries of the corresponding observation mask element are blocked from reaching the sensor.

12. The method according to claim 11, wherein the light source is a white LED, or a combination of a number of colored LEDs, that emits a wide color spectrum.

13. The method according to claim 11, wherein the projection mask and/or the observation mask comprises a checkerboard-like pattern, wherein the projection mask elements and/or the observation mask elements are disposed adjacent to one another without gaps.

* * * * *